US007289879B2

(12) United States Patent
William et al.

(10) Patent No.: US 7,289,879 B2
(45) Date of Patent: *Oct. 30, 2007

(54) PILL DISPENSING SYSTEM

(75) Inventors: Jeffrey P. William, Dry Prong, LA (US); Galina Potepalov, Pineville, LA (US); Allan Dolores, Carrollton, GA (US); Michael Bergeron, Pineville, LA (US)

(73) Assignee: Parata Systems, LLC, Morrisville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/384,648

(22) Filed: Mar. 20, 2006

(65) Prior Publication Data

US 2006/0161293 A1    Jul. 20, 2006

Related U.S. Application Data

(63) Continuation of application No. 10/867,142, filed on Jun. 14, 2004, now Pat. No. 7,016,766, which is a continuation of application No. 10/655,226, filed on Sep. 4, 2003, now Pat. No. 6,775,589, which is a continuation of application No. 10/233,807, filed on Sep. 3, 2002, now Pat. No. 6,681,149, which is a continuation of application No. 09/768,200, filed on Jan. 23, 2001, now abandoned, which is a continuation of application No. 09/205,246, filed on Dec. 4, 1998, now Pat. No. 6,176,392, which is a continuation-in-part of application No. 08/986,665, filed on Dec. 8, 1997, now Pat. No. 6,036,812, which is a continuation-in-part of application No. 08/986,247, filed on Dec. 5, 1997, now Pat. No. 6,006,946.

(51) Int. Cl.
*G06F 17/00* (2006.01)

(52) U.S. Cl. ............... 700/235; 700/216; 700/231; 700/245; 221/2; 221/7; 221/10; 221/17; 221/107

(58) Field of Classification Search ......... 700/231–244
See application file for complete search history.

(56) References Cited

U.S. PATENT DOCUMENTS

| 2,002,753 A | 5/1935 | Parks et al. |
| 2,442,025 A | 5/1948 | Smith |
| 3,045,864 A | 7/1962 | Hurst et al. |
| 3,170,627 A | 2/1965 | Pearson et al. |

(Continued)

FOREIGN PATENT DOCUMENTS

| WO | WO 95/25423 A2 | 9/1995 |
| WO | WO 95/25423 A3 | 9/1995 |

*Primary Examiner*—Gene O. Crawford
*Assistant Examiner*—Michael K. Collins
(74) *Attorney, Agent, or Firm*—Myers Bigel Sibley & Sajovec

(57) ABSTRACT

A pill dispensing system includes a shelving unit in array form that holds a number of bulk containers, each holding a bulk amount of a pill to be dispensed. A computer controlled robot removes a selected bulk container and places it on a counter that also dispenses pills. The robot has an arm with a free end portion that can grip a bulk container or a single pill bottle to be filled. The robot is computer controlled to retrieve an empty pill bottle, place it on a label printing and applying unit, then place it next to the counter/dispenser to receive the selected number of selected prescription pills, then place the filled, labeled bottle on a conveyor. In an alternate embodiment, pill bottles are dispensed from a dispenser that holds bottles on inclined plates and feeds them to a vertical dispensing channel. Gates prevent the flow of bottles from an inclined position until the plate above has been emptied.

15 Claims, 12 Drawing Sheets

U.S. PATENT DOCUMENTS

| | | |
|---|---|---|
| 3,194,431 A | 7/1965 | Garvin |
| 3,215,310 A | 11/1965 | Hurst et al. |
| 3,266,664 A | 8/1966 | Pearson et al. |
| 3,368,713 A | 2/1968 | Hurst et al. |
| 3,837,139 A | 9/1974 | Roseberg |
| 3,938,700 A | 2/1976 | Camp et al. |
| 4,111,332 A | 9/1978 | Hurst et al. |
| 4,171,065 A | 10/1979 | Hurst |
| 4,232,800 A | 11/1980 | Martin et al. |
| 4,303,179 A | 12/1981 | Spring |
| 4,812,629 A | 3/1989 | O'Neil et al. |
| 4,869,394 A | 9/1989 | Hurst |
| 4,878,705 A | 11/1989 | Arnquist |
| 5,080,256 A | 1/1992 | Rockola |
| 5,133,632 A | 7/1992 | Aramaki et al. |
| 5,143,193 A | 9/1992 | Geraci |
| 5,208,762 A | 5/1993 | Charhut et al. |
| 5,277,534 A | 1/1994 | Anderson et al. |
| 5,337,919 A | 8/1994 | Spaulding et al. |
| 5,348,061 A | 9/1994 | Riley et al. |
| 5,468,110 A | 11/1995 | McDonald et al. |
| 5,588,688 A | 12/1996 | Jacobsen et al. |
| 5,593,267 A | 1/1997 | McDonald et al. |
| 5,671,592 A | 9/1997 | Yuyama et al. |
| 5,812,410 A | 9/1998 | Lion et al. |
| 5,838,575 A * | 11/1998 | Lion ............................ 700/231 |
| 5,852,911 A | 12/1998 | Yuyama et al. |
| 5,873,488 A | 2/1999 | Guerra |
| 5,884,806 A | 3/1999 | Boyer et al. |
| 5,897,024 A | 4/1999 | Coughlin et al. |
| 5,907,493 A | 5/1999 | Boyer et al. |
| 5,946,883 A | 9/1999 | Yuyama et al. |
| 5,964,374 A | 10/1999 | Yuyama et al. |
| 6,006,946 A * | 12/1999 | Williams et al. ................. 221/9 |
| 6,036,812 A * | 3/2000 | Williams et al. ............. 156/277 |
| 6,176,392 B1 * | 1/2001 | William et al. .............. 221/109 |
| 6,681,149 B2 * | 1/2004 | William et al. .............. 700/231 |
| 6,775,589 B2 * | 8/2004 | William et al. .............. 700/216 |
| 7,016,766 B2 * | 3/2006 | William et al. .............. 700/216 |

* cited by examiner

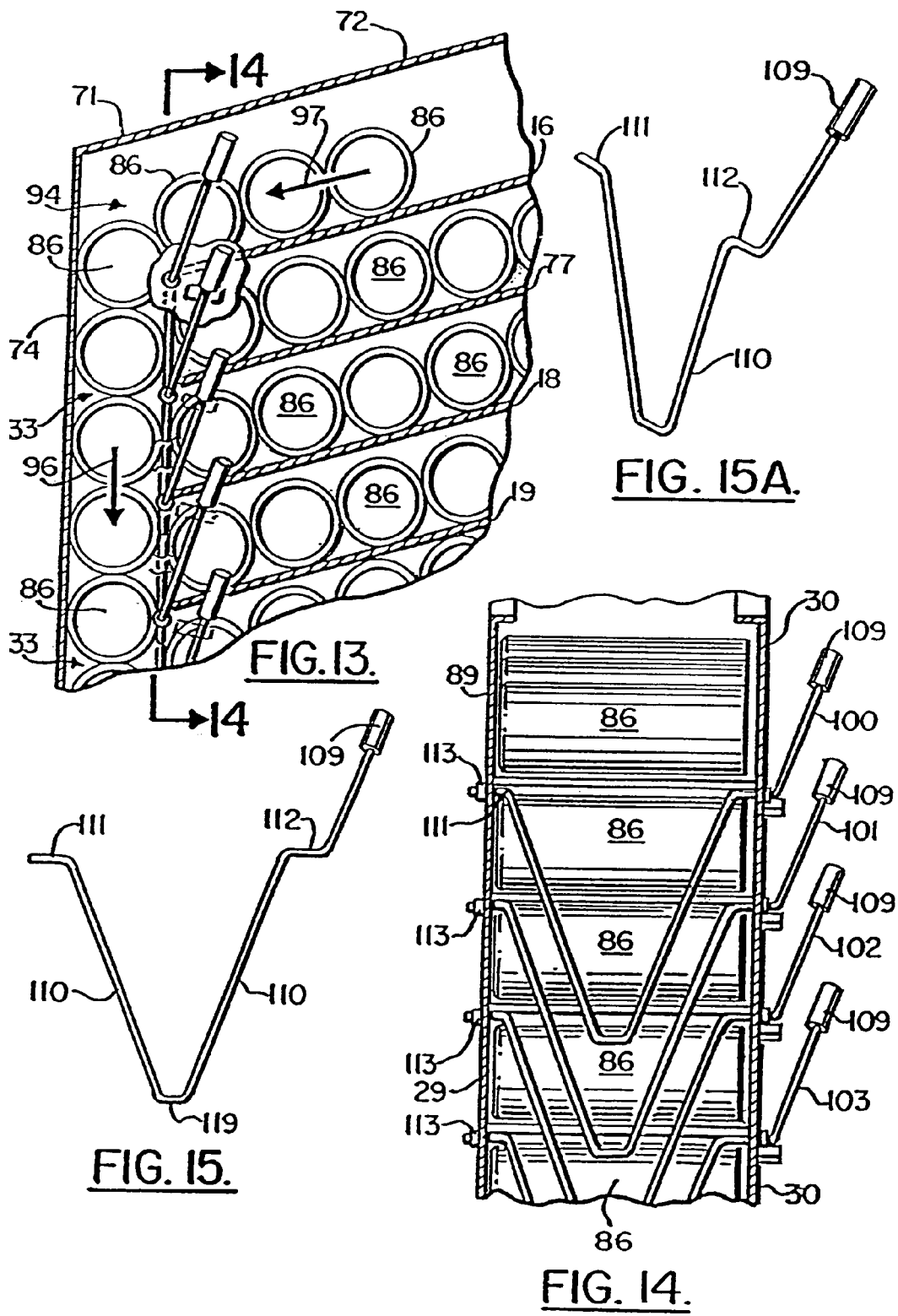

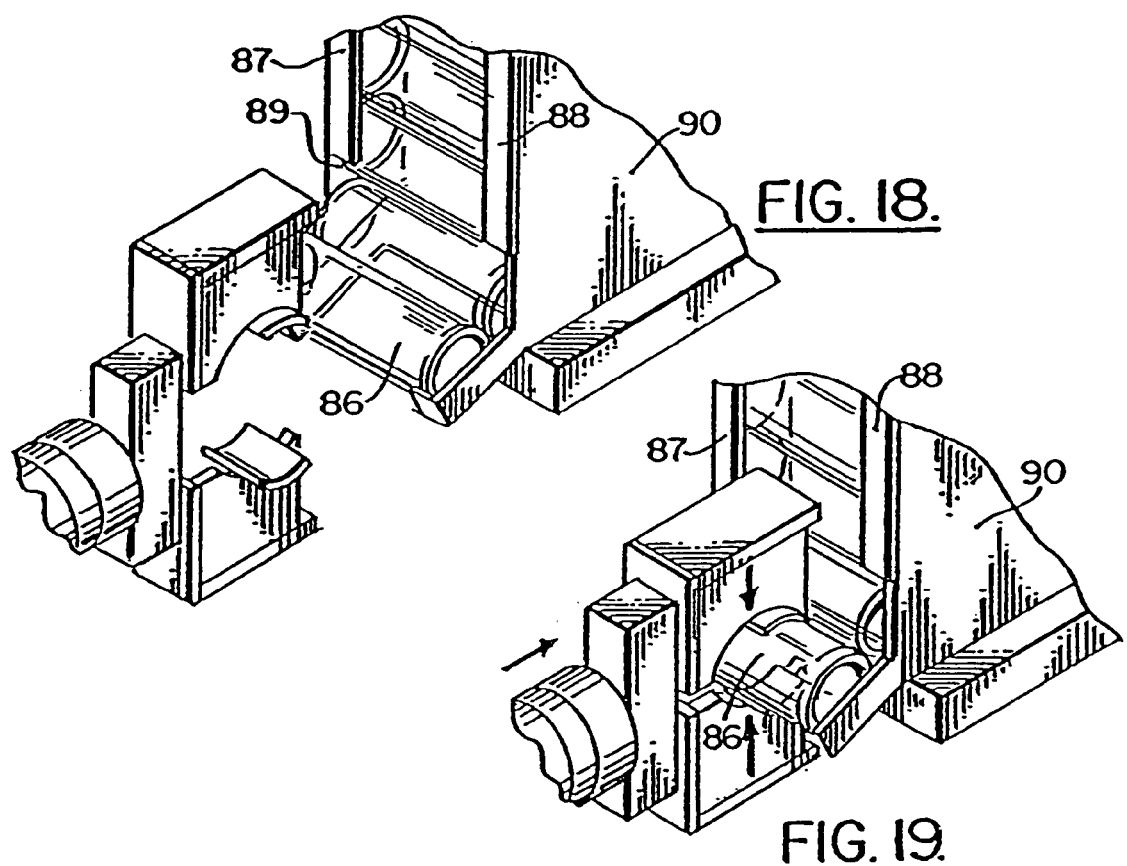
FIG. 18.
FIG. 19.
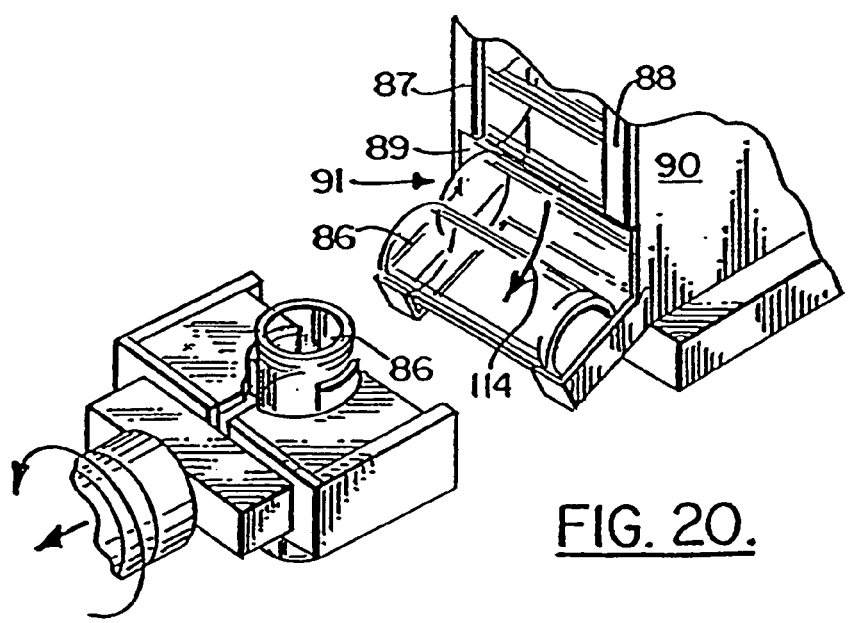
FIG. 20.

PILL DISPENSING SYSTEM

CROSS-REFERENCE TO RELATED APPLICATIONS

This application is a continuation of U.S. patent application Ser. No. 10/867,142 filed Jun. 14, 2004. now U.S. Pat. No. 7,016,766, which is a continuation of U.S. patent application Ser. No. 10/655,226, filed Sep. 4, 2003 now U.S. Pat. No. 6,775,589, which is a continuation of U.S. patent application Ser. No. 10/233,807, filed Sep. 3, 2002, now U.S. Pat. No. 6,681,149, which is a continuation of U.S. patent application Ser. No. 09/768,200, filed Jan. 23, 2001 now abandoned, which is a continuation of U.S. patent application Ser. No. 09/205,246, filed Dec. 4, 1998, now U.S. Pat. No. 6,176,392, which is a continuation-in-part of U.S. patent application Ser. No. 08/986,665, filed Dec. 8, 1997, now U.S. Pat. No. 6,036,812, which is a continuation-in-part of U.S. patent application Ser. No. 08/986,247, filed Dec. 5, 1997, now U.S. Pat. No. 6,006,946, which are all incorporated herein by reference.

FEDERALLY SPONSORED RESEARCH OR DEVELOPMENT

Not applicable.

REFERENCE TO A "MICROFICHE APPENDIX"

Not applicable.

BACKGROUND OF THE INVENTION

1. Field of the Invention

The present invention relates to systems for automatically filling prescriptions, and more particularly to a computer controlled system for dispensing containers (e.g., pill bottles) and then filling the bottles with pills, wherein a robotic arm removes bulk containers one at a time and then fills a selected bottle with a selected number of pills from the selected bulk container.

2. General Background of the Invention

In the pharmaceutical industry, many different types of pills must be quickly dispensed into pill bottles in order to efficiently provide prescription services to patients. Several such systems have been patented that disclose devices attempting to automate pill prescription services.

Kerney Hurst is a named inventor of a number of issued and now expired U.S. patents that deal with counting articles such as pills from a cassette or drum.

dispensed. The cassettes of the Hurst '394 patent cooperate with a counter/dispenser having a motor drive that rotates a drum inside the cassette to dispense and count pills contained in the drum. A selected pill in a selected cassette is placed upon the motor drive when a prescription is to be filled. The druggist then selects a number of pills using a numeric key pad entry. The druggist also selects a desired size pill bottle and places that pill bottle under the counter/dispenser so that when the motor drive rotates the drum contained within the cassette, the desired number of pills are dispensed from the cassette through the counter/dispenser and into the pill bottle.

Recent patents deal with the concept of automating the process of filling a prescription. These include U.S. Pat. Nos. 5,208,762 and 5,337,919. The '762 patent, issued to Charhut et al., discloses a method and apparatus for dispensing drugs, wherein a patient's order of one or more prescriptions is automatically filled. Various drugs are stored in three or more filler lines. A vial size is assigned to each line. When a prescription is filled, it is automatically assigned to a line in view of the vial size requirements and processed accordingly. Provisions are made for the inability to fill a prescription or order. Subsequently, all of the patient's prescriptions are collected and made available as a single order.

U.S. Pat. No. 5,337,919, issued to Spaulding et al., discloses an automatic prescription dispensing system that includes a housing or flame having a plurality of pill dispenser units mounted therein, a plurality of vial supply assemblies at one end of the housing, and a filled vial off load carousel at an opposite end. A vial manipulator assembly is mounted on the housing to enable translational movement of a vial manipulator frame vertically and horizontally and pivoting about a vertical axis to retrieve vials from the supply assemblies, fill the vials at the dispenser units, and deposit the filled vials onto the carousel. The vial manipulator frame includes spring loaded grippers to engage and carry the vials and a drive motor and gear for meshing with dispenser unit gears to operate the dispenser units. The system includes a controller including an interface for coupling to the printer port of a pharmacy host computer printer port for intercepting drug name and quantity data for a prescription which was directed to a prescription label printer. Such prescription data is used by the controller for selecting the dispenser unit having the required drug, vial size, and number of pills to be dispensed.

Some automated drug filling systems automatically fill a prescription and even apply a cap to the pill bottle. These are typically very expensive devices that are only justifiable to very large end users such as hospitals.

| Patent | Issued Date | Filing Date | Title | Expiration Date | Inventors |
|---|---|---|---|---|---|
| 3,045,864 | Jul. 24, 1963 | Jan. 25, 1959 | "Article Counting Device" | Jul. 24, 1979 | Hurst/Pearson |
| 3,170,627 | Feb. 23, 1965 | Jul. 08, 1963 | "Article Counting Device" | Feb. 23, 1983 | Pearson/Hurst |
| 3,215,310 | Nov. 02, 1965 | Jul. 03, 1963 | "Article Counting Device" | Nov. 02, 1982 | Hurst/Pearson |
| 3,266,664 | Aug. 16, 1966 | Jun. 09, 1965 | "Article Counting Device" | Aug. 16, 1983 | Pearson/Hurst |
| 3,368,713 | Feb. 13, 1968 | Aug. 15, 1966 | "Article Counting Device" | Feb. 13, 1985 | Hurst/Pearson |
| 4,111,332 | Sep. 05, 1978 | Dec. 16, 1974 | "Article Counting Device" | Sep. 05, 1995 | Hurst/Pearson |
| 4,171,065 | Oct. 16, 1979 | Dec. 06, 1976 | "Circuitry And System For Controlling Multi-Use Article Dispensing Cells" | Oct. 16, 1996 | Hurst |

A more recent Kerney Hurst patent is U.S. Pat. No. 4,869,394 which relates to a cassette for holding pills to be There is a need for an automated prescription filling system that includes a bottle dispenser that can be used by smaller and medium sized users such as pharmacies as opposed to very large hospitals.

There is also a need for a container (e.g., pill bottle) dispensing system that uses a cabinet or shelving unit that holds storage containers that can quickly and automatically access a container for subsequent filling (e.g., with a selected pill).

BRIEF SUMMARY OF THE INVENTION

The present invention provides a method and apparatus for automatically dispensing containers such as bottles for prescription medication. The system produces a label and fills prescription vials with a specific drug for a specific patient. The system includes a "cassette" based pill counting system and a label printer serviced by an articulated robotic manipulator whose functions are coordinated by a computer to extemporaneously label and fill prescription vials.

A record of prescription information is received by the controlling computer from a pharmacy order entry computer. This record includes usual prescription label information such as patient name, doctor name, instructions, etc. as well as drug and quantity information.

The controlling computer directs a robotic manipulator to retrieve a drug storage unit which includes a queuing and separating means (i.e., cassette).

The controlling computer sends the drug and quantity information to a control counter/dispenser which will cooperate with the drug storage cassette to count and dispense the required number of pills. The robotic manipulator arm places the cassette on a counter, and a bar code on the cassette is read by a scanner interfaced to the counter. If the bar code matches the drug information, the counting and dispensing system is activated and pills are dispensed to a temporary holding volume.

While the pills are being counted the robotic manipulator arm retrieves an empty vial from a vial dispenser. The manipulator then places the vial on a vial rotating device which is positioned in a manner so that the prescription label is applied to the label to the vial as it is printed. The robotic manipulator then retrieves the labeled vial from the labeler and maneuvers the vial to the temporary pill holding volume. Then robotic manipulator lifts a gate allowing the pills to fall from the holding volume into the vial.

The manipulator then places the filled vial to a conveyor means and releases it. The conveyor then transports it to an operator for checking and delivery to the patient.

The robotic manipulator then retrieves the cassette from the counter and returns the cassette to its shelf. When a cassette requires replenishment of its stock, the manipulator retrieves the cassette from its storage shelf and places it in an output holding area that is accessible by a system operator. The operator removes the cassette from the output holding area and performs the replenishment steps. The cassette is returned to service by placing it in an input holding area. The manipulator then returns the cassette to its storage shelf. Multiple vial sizes are accommodated by the single robotic manipulator.

The present invention thus provides an improved method and apparatus for filling prescriptions. The method of the present invention provides a storage shelving unit that can be an array having a plurality of shelves arranged in vertical columns for storing a plurality of bulk containers. Each respective container contains and stores a bulk quantity (e.g., 100 to 2000 pills) of a selected pharmaceutical to be dispensed.

A robotic, computer controlled arm is used to grasp a selected one of the containers that has the correct pills for the prescription to be filled.

The selected container is then removed from its receptacle with the robot arm and then placed by the robot arm on a counter/dispenser.

Pills are then dispensed in a correct number from the container by the counter and into a pill bottle that is also supported by the robot arm. Dispensing of the pills can be suspended until the robot arm has grabbed a pill bottle and placed it under the discharge chute of the counter/dispenser. The counter/dispenser then counts and dispenses the pills.

With the method of the present invention, the robotic arm then removes the container from the counter/dispenser and returns it to its receptacle.

The method of the present invention further comprises the step of using a computer to control the robotic arm during movement of the bulk container and pill bottle.

In the method of the present invention, the pill bottle is moved from a pill bottle dispenser to a labeling machine and then to the counter/dispenser.

The method of the present invention further comprises the step of moving the pill bottle to a conveyor after it has been filled so that the pharmacist can check the prescription and cap the bottle.

The method of the present invention includes the step of arranging the bulk containers and receptacles in an array having a curved front in which the robotic arm rotates in order to access the receptacles.

The method of the present invention includes the step of controlling the counter with a computer so that a pharmacist sitting at a computer console can direct movement of the robotic arm to: 1) select a desired bulk container, 2) place that container on the counter/dispenser, 3) retrieve a pill bottle of selected size, 4) place a label on a pill bottle, 5) dispense the selected number of pills from the counter/dispensing unit into the pill bottle; and 6) place the pill bottle on a conveyor.

The apparatus of the present invention thus provides an improved apparatus for filling prescriptions. The apparatus includes a shelving unit defining an array of storage containers, each container having an interior for holding a bulk amount of a selected pill product.

Each container is removable from the shelving unit, having a receptacle that separates each container from the next container. A computer controlled robotic arm reaches and grips a selected container and removes it from its receptacle. The computer controlled robotic arm has a free-end portion that grips the container to transport it to a counter.

A counter receives the selected container, the counter being computer controlled to dispense a selected number of pills therefrom into a bottle.

The free-end portion of the robotic arm has first and second gripping portions that can selectively grip a selected container or a selected pill bottle respectively.

The present invention provides a shelving unit that is curved in shape along its front surface.

The containers are arranged in an array that is accessed by the robotic arm when the robotic arm rotates about a center of rotation. The shelving unit has a curved shape that conforms to the movement of the robotic arm free end as the robot rotates about its center of rotation.

The robotic arm can move its free end portion into multiple and different elevational positions such as when removing a container from a higher or lower shelf.

The shelving unit preferable comprises a plurality of vertical columns, each column having a plurality of vertically spaced apart shelves for holding containers in an aligned vertical column.

Each column has a front face that is perpendicular to a radial line that extends radially from the center of rotation of the robotic arm.

The free-end portion of the robotic arm includes a pair of opposed gripping surfaces that move between opened and closed positions. The free-end portion of the robotic arm includes a pair of opposed jaws that are specially shaped to grip either the container or the pill bottle.

The free-end portion of the robotic arm has a gripping surface portion that includes a pair of opposed jaws with a first pair of shaped surfaces thereon for gripping one of the selected bulk containers and a second pair of surfaces that are curved for engaging the sides of a pill bottle to be handled during the pill dispensing procedure.

The shelving unit includes a plurality of shelf surfaces that can be inclined upon which the containers are supported.

A counter/dispenser or counting unit is spaced circumferentially away from the shelving unit. The robotic arm rotates away from the shelving unit to the counter/dispenser during use. The robotic arm moves its free end portion along a path that enables changes of elevation for both the free-end portion of the robotic arm and the supported container the robotic arm places the selected cassette or container on the counting unit. A selected number of pills are dispensed into a chute of the counting unit.

A bottle dispenser can be provided for holding a plurality of bottles to be filled with prescriptions. The bottle dispenser present a selected pill bottle for filling and the robotic arm enables its free end portion to move to a bottle gripping position at the bottle dispenser and from there to a bottle labeler and then to a filling position next to the counter/dispenser. The bottle can be of multiple bottle sizes to be selected on demand. The vials or bottles may be retrieved from a device that holds them in an ordered orientation. A labelling step may be interjected before placing the vial next to the counter/dispenser.

An alternate embodiment of the apparatus of the present invention provides an alternate bottle dispensing construction. The alternate construction of the bottle dispenser includes a frame having a supporting base with a pair of side walls with a space therebetween and a bottle dispensing opening at the bottom of the frame. A plurality of inclined plates are positioned in between the side walls and supported by the frame, each of the plates being sized to carry a plurality of bottles to be dispensed. The inclined orientation of the plates enables the bottles to move toward the front of the frame under the influence of gravity.

The frame provides a dispensing channel for dispensing bottles from an upper end portion of the frame to a lower end portion of the frame and to a dispensing opening. A plurality of gates, one at the end of each of the inclined plates control the flow of bottles from one or more plates to the channel. Each gate is movable between an open and closed position.

Each of the gates has a counter weight that urges the gate into an opened position. The gates are configured to open when the inclined plate above the gate has been emptied of bottles. The frame has a dispensing outlet at the front bottom of the frame for dispensing bottles from the dispensing channel one at a time.

A conveyor can be provided for receiving pill bottles that have been labeled and filled with a prescription.

The robotic arm enables its free-end portion to move a pill bottle from a position next to the counter during filling to a position on the conveyor once it is filled with the selected prescription.

BRIEF DESCRIPTION OF THE SEVERAL VIEWS OF THE DRAWING(S)

For a further understanding of the nature, objects, and advantages of the present invention, reference should be had to the following detailed description, read in conjunction with the following drawings, wherein like reference numerals denote like elements and wherein:

FIG. 13 is a fragmentary elevational view of the alternate embodiment of the apparatus of the present invention;

FIG. 14 is a sectional elevational view taken along lines 14-14 of FIG. 13;

FIG. 15 is a fragmentary elevational view of the alternate embodiment of the apparatus of the present invention;

FIG. 15A is a perspective fragmentary view of the alternate embodiment of the apparatus of the present invention;

FIG. 18 is a partial perspective view of the alternate embodiment of the apparatus of the present invention illustrating the transfer of a pill bottle from the dispenser by the robotic arms;

FIG. 19 is a perspective fragmentary view of the alternate embodiment of the apparatus of the present invention showing a gripping of a pill bottle to be dispensed by the robotic arm; and FIG. 20 is a fragmentary perspective view of the alternate embodiment of the apparatus of the present invention showing the robotic arm after it has removed a pill bottle from the dispenser.

DETAILED DESCRIPTION OF THE INVENTION

Figure 1:
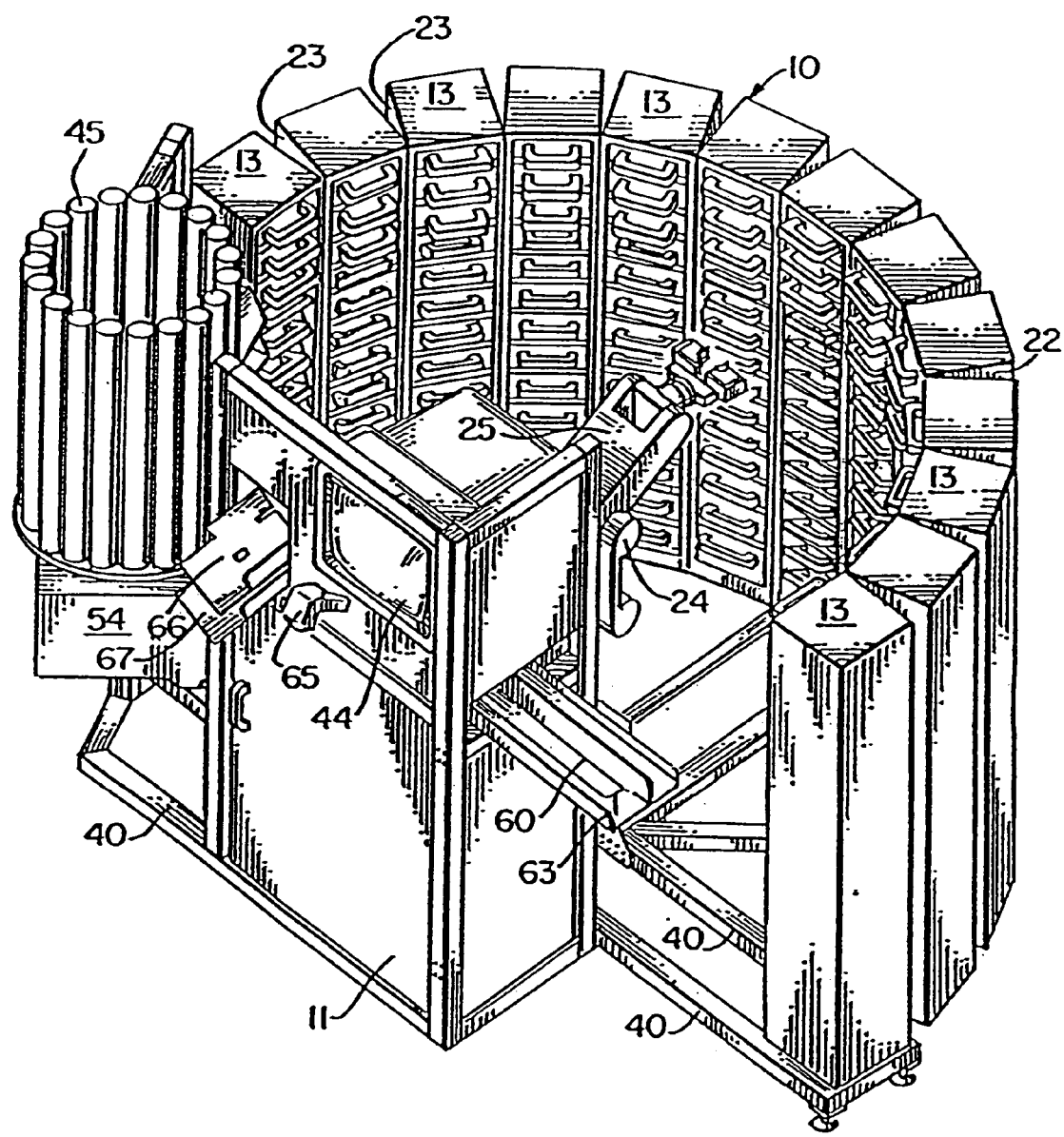
FIG. 1 is a perspective view of the preferred embodiment of the apparatus of the present invention.
Figure 4:
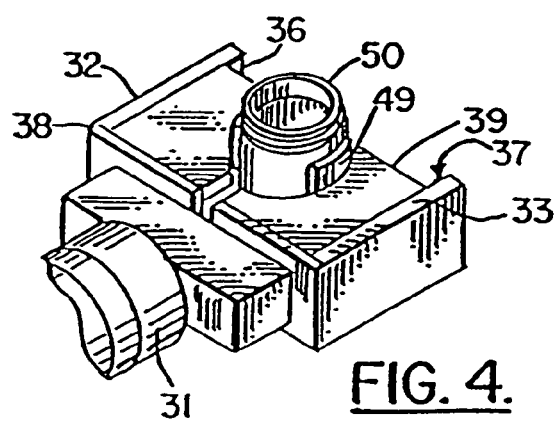
FIG. 4 is a perspective fragmentary view of the preferred embodiment of the apparatus of the present invention showing the robotic arm free-end portion gripping a pill bottle to be filled.
Figure 5:
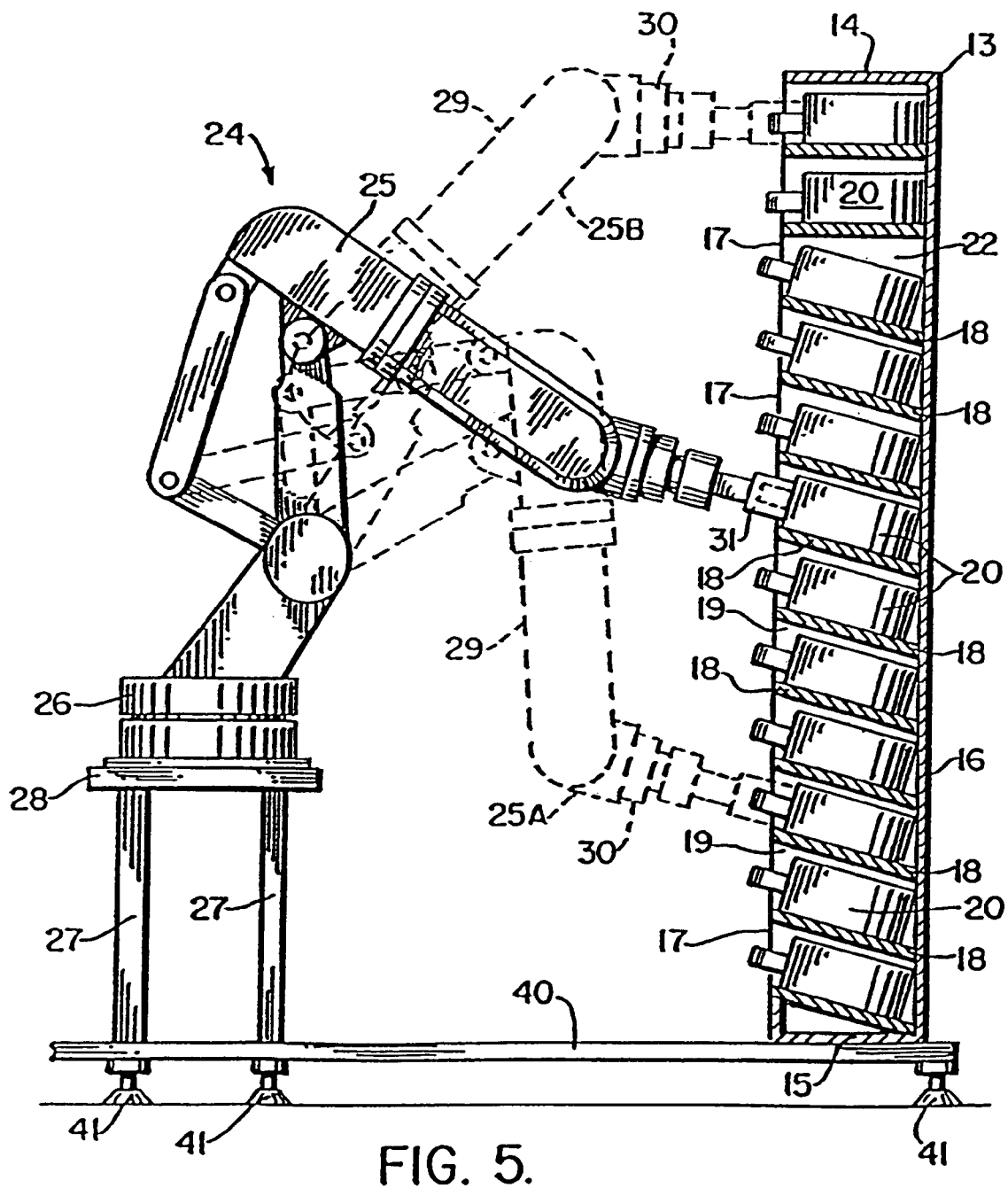
FIG. 5 is an elevational fragmentary view of the preferred embodiment of the apparatus of the present invention showing the robotic arm accessing bulk containers at different levels of one column of the array of the shelving unit.
Figure 6:
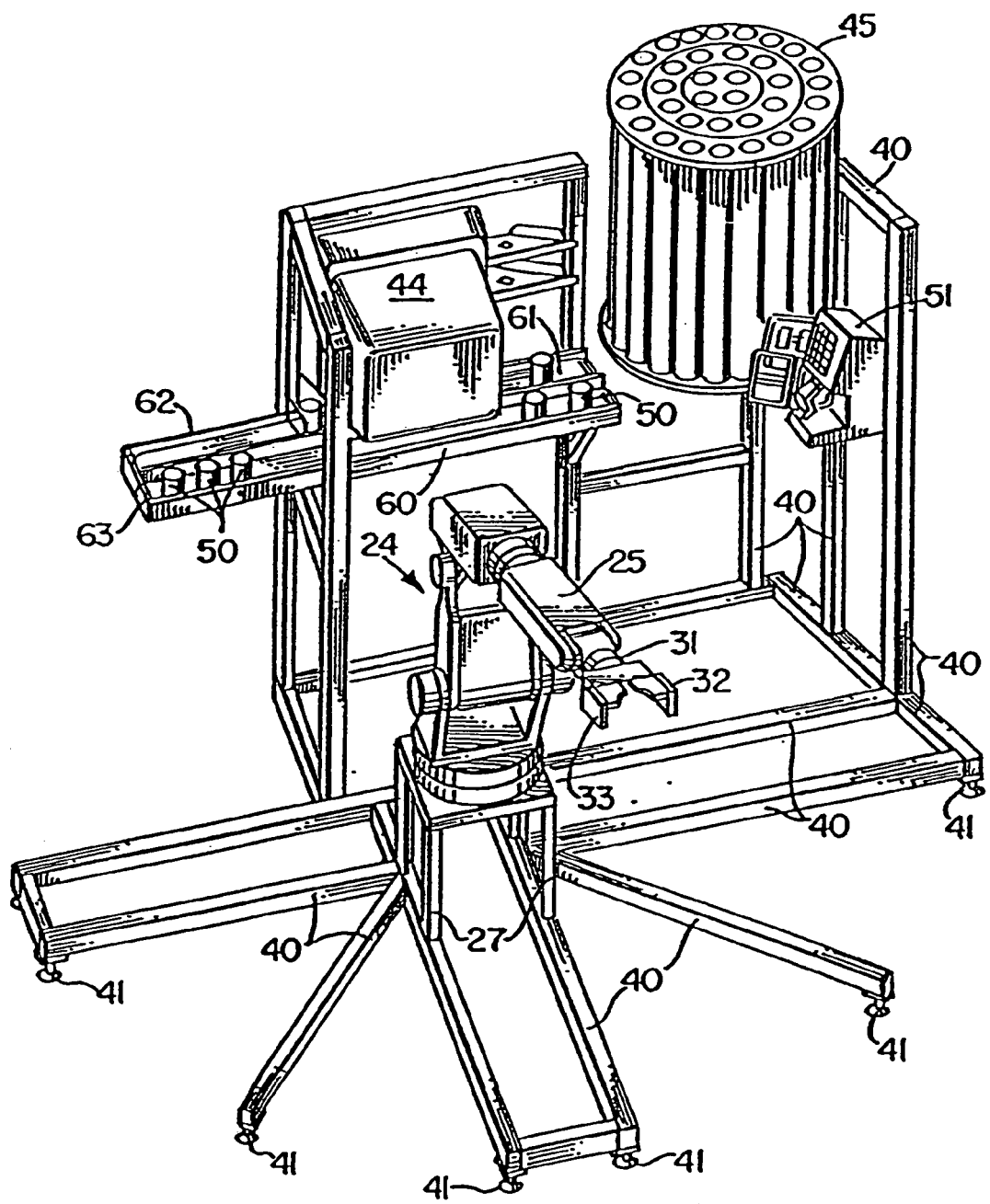
FIGS. 6-6A are a partial perspective view of the preferred embodiment of the apparatus of the present invention shown with the array of shelves removed.
Figure 6A:
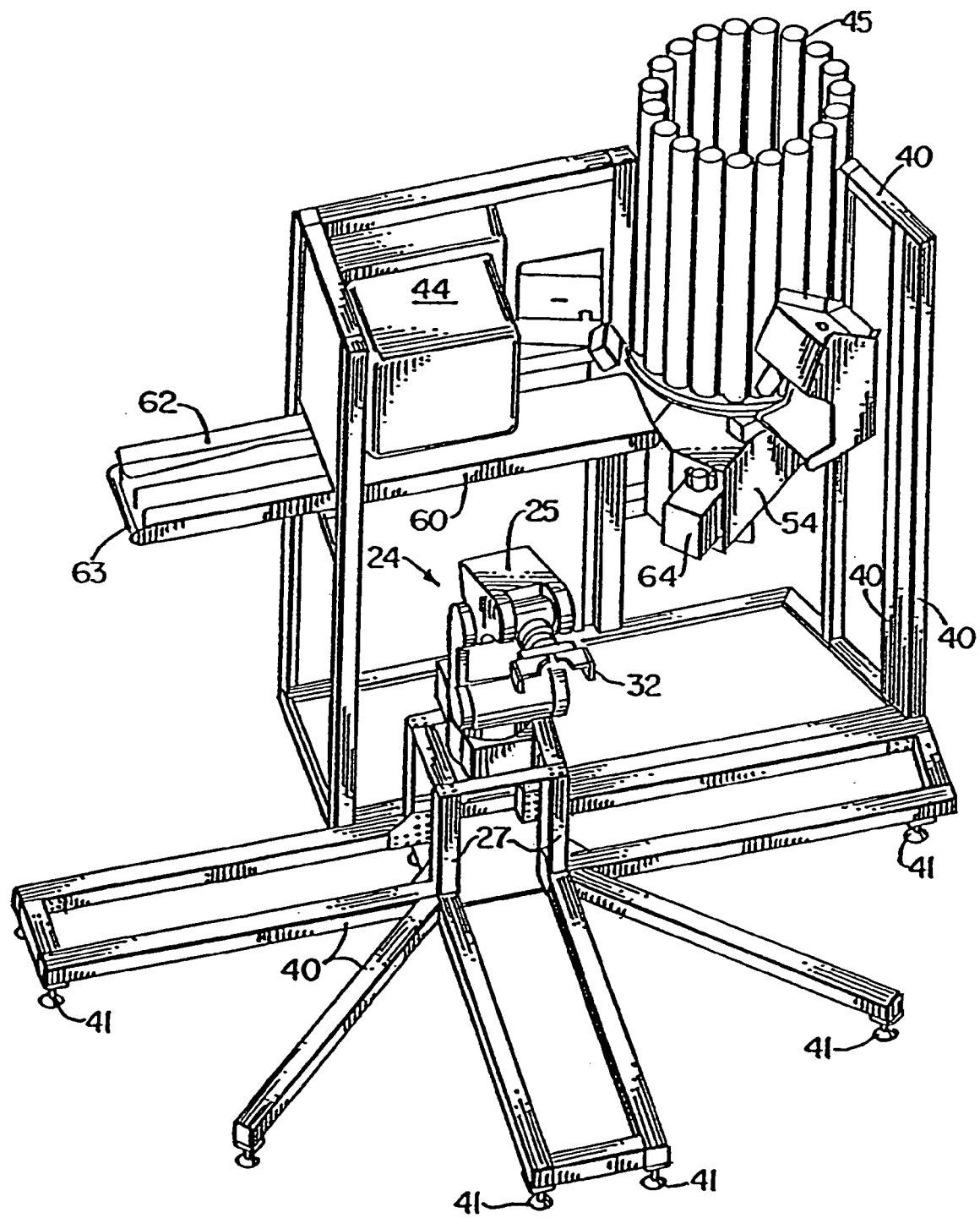

FIGS. 1-6 show the preferred embodiment of the apparatus of the present invention, designated generally by the numeral 10 in FIG. 1. In FIGS. 1 and 6, pill dispensing apparatus 10 includes generally the various components supported on frame 40, an operator's console 11, a shelving unit 12, robot 24, and a frame 40. Frame 40 supports shelving unit 12, console 11, robot 24, a label printing and applying device 54, and a counter/dispenser 60, and pill bottle dispenser 45.

Frame 40 can be provided with a plurality of feet 41 for engaging an underlying surface, shop floor, concrete slab, or the like.

Shelving unit 12 is seen in FIGS. 1 and 5. The shelving unit 12 includes a plurality of vertically extending column members 13 each having a top panel 14, a bottom panel 15, a rear panel 16, and side walls 22, 23.

A generally flat front surface 17 is provided to each column 13 as defined by the front edge of side walls 22, 23 and the front edge of shelves 18. The shelves 18 in combination with side walls 22, 23 define receptacles 19 for receiving bulk containers 20.

The bulk containers 20 can be a cassette type container having a rotary drum contained therein and a handle 21 for manipulating the bulk container. The rotating drum has a slotted disk that cooperates with the counter/dispenser to count and dispense the pills. Such bulk containers 20 are in commercial use, being marketed by Automated Prescription Systems, Inc. of Alexandria, La. and shown, for example, in U.S. Pat. No. 4,869,394 incorporated herein by reference.

Other counting device bulk containers such as the Drug-O-Matic sold by Automated Prescription Systems, Inc. or the ATC212 cassette sold by Baxter International of Deerfield, Ill. could be used. The bulk containers 20 would be used to contain different kinds of pills. For example, a single container 20 might contain Seldane™. The next individual container might contain Augmentin™, etc. Typically, these bulk containers 20 would contain 100-2000 pills whereas a typical prescription might fill a bottle with 20 or 30 pills. Cassettes 20 thus fulfill two functions. One is to store a stock quantity of pills from which a specific patient quantity can be counted. The other function is to cooperate with the counting head 51 to queue and separate the pills for counting and dispensing. The essence of the counting method is a slotted disk that rotates at an angle. The cassette is designed with a handle which makes it easily manipulated by the robot 24 or a human. Each of the cassettes 20 may be removed singly from its storage shelf and maneuvered to the counting head. When a cassette 20 requires replenishment, the robot 24 transports it from its storage shelf to a "replenish out" shelf 66. The operator retrieves it from there and performs necessary replenishment activities on it. When finished, the operator places it in the "replenish in" port 67 where a bar code on the cassette is automatically scanned with scanner 65. Based on the bar code data, the robot retrieves the cassette and returns it to the storage shelf.

A robot 24 provides a robotic arm 25 that can rotate about its pedestal 26 into different rotational positions. As shown in FIG. 5, the robotic arm 25 has a free-end portion 31 that can move into different elevational positions such as the lower elevational position 25A shown in phantom lines in FIG. 5 and the higher elevational position shown in phantom lines 25B in FIG. 5. The free end 31 can also change in radial position and attitude. This combination of rotational movement of the robotic arm 25 and the different elevational positions of its free-end 31 enables the free-end portion 31 to grip and retrieve any selected bulk container 20 by grasping the handle 21 portion thereof as will be explained more fully hereinafter. A computer can be controlled to activate movement of the robotic arm 25 and its free-end portion 31, particularly the jaws 32, 33 thereof.

Robot 24 can be a commercially available robot, being manufactured and sold by Motoman Corporation of West Carrolton, Ohio, for example. Such a robot 24 and its robotic manipulator arm 25 has multiple arm segments 29, 30. The pedestal 26 provides a rotating connection that enables the robotic arm 25 to rotate with respect to horizontal support surface 28. The horizontal support 28 can be supported by a vertical frame 27 portion of frame 40 as shown in FIGS. 5 and 6. The robotic manipulator arm 25 is able to repeat certain maneuvers in space according to the command input and place the free end portion or gripping means 31 in a 3-dimensional space with variable attitudes (angles) about three orthogonal axes. The robot 24 performs five primary functions: 1) move cassette 20 from its storage shelf 18 to the counter 51 and vise-a-versa 2) move the empty prescription vial 50 from the vial storage 45 and to the label applier 64; 3) move the labeled vial 50 to the temporary holding volume of the counting head 51 for transfer of the pills into the vial 50; 4) move the filled vial 50 to the off-load conveyor 60; and 5) move cassettes 20 between the replenishment ports 66, 67 and the cassette storage shelves 12.

Figure 2:
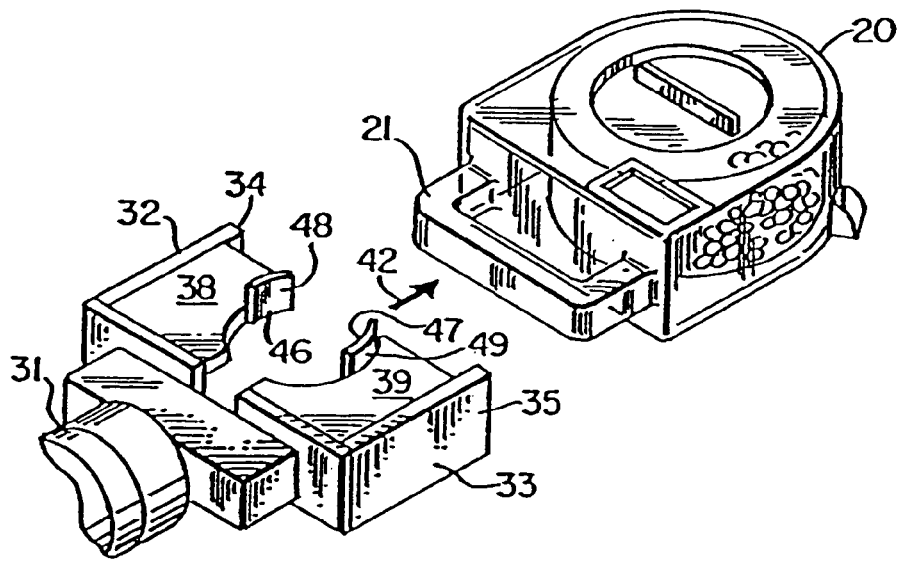
FIG. 2 is a fragmentary view of the preferred embodiment of the apparatus of the present invention showing the bulk container and free-end portion of the robotic arm just prior to a gripping of the bulk container with the free-end portion of the robotic arm.
Figure 3:
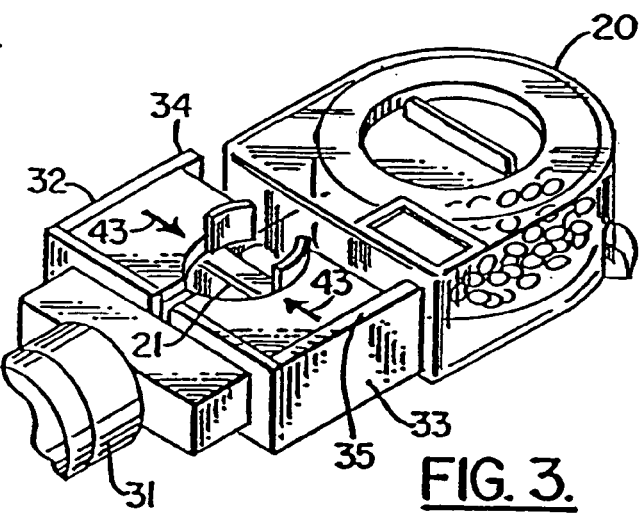
FIG. 3 is a perspective fragmentary view of the preferred embodiment of the apparatus of the present invention shown during a gripping of the bulk container with the free-end portion of the robotic arm.

In FIGS. 2-4, the free-end portion 31 of robotic arm 25 is shown more particularly, including moving jaws 32, 33 that can be used to grip either container 20 or pill bottle 50. In FIG. 2, the jaws 32, 34 provide respective side wall portions 34, 35. Each of the side walls 34, 35 provides a flat inside surface that is used to engage the handle 21 as shown in FIGS. 2 and 3. The side wall 34 provides a flat inside surface 36. The side wall 35 provides a generally flat inside surface 37.

These surfaces 36, 37 engage handle 21 when the jaws 32, 34 move to a closed position. Horizontal plate 38 is attached to side wall 34 by welding, for example. Likewise, the horizontal plate 39 is attached to side wall 35 by welding, for example. The horizontal plates 38, 39 are each provided with an arc-shaped section 46, 47 respectively for conforming to the outer surface of a cylindrically-shaped pill bottle 50 as shown in FIGS. 2 and 4. The arc shaped sections 46, 47 have curved walls 48, 49 respectively. In FIG. 4, the pill bottle 50 has been gripped by the arc-shaped surfaces 46, 47 of plates 38, 39 and by curved walls 48 and 49 that are attached thereto by welding for example.

Arrow 42 in FIG. 2 illustrates the forward movement of free-end portion 31 of robotic arm 25 when a container 20 is to be removed from a receptacle 19 of shelving unit 12. Arrows 43 in FIG. 3 illustrate that jaws 32, 33 can be moved between a closed or gripping position and an outer, open position. The open position of jaws 32, 33 is used when the free-end portion 31 has not yet gripped the container 21, but is attempting to do so. The closed position of jaws 32, 33 is used (FIG. 3) when the handle 21 of container 20 is to be gripped. In FIG. 4, the closed position of jaws 32, 33 is shown wherein pill bottle 50 has been gripped between curved walls 48, 49 and arcuate surfaces 46, 47 of jaws 32, 33.

In FIGS. 1-6, a computer 44 can be used for controlling the movement of robotic arm 25, and the dispensing of pills from a selected container 20 through a counter/dispenser or counting head 51. Counter/dispensers are known in the art such as those shown and described in U.S. Pat. Nos. 4,111,332 and 4,869,394. Its function is coordinated to count a specific quantity for a specific prescription when the proper cassette is placed on the counting head. It also includes a temporary storage volume from which the pills will be retrieved.

Movement of the robotic arm 25 is computer controlled into both rotational and elevational positions as shown in FIG. 5. The computer 44 controls the operation of the robotic arm 25 to grab a pill bottle 50 from pill bottle dispenser 45. The robotic arm places the pill bottle 50 on label printer and applier 54 so that a prescription label with desired patient and prescription information can be included on the label that is printed and applied to the bottle 50. The computer 44 sends label information such as patient name, drug and instructions to the label printer. Additionally, the discharge of pills from container 20 through counter/dispenser 51 can be controlled with computer 44. The computer 44 also controls the arm 25 to place a filled bottle 50 on conveyor 60.

Figure 7:
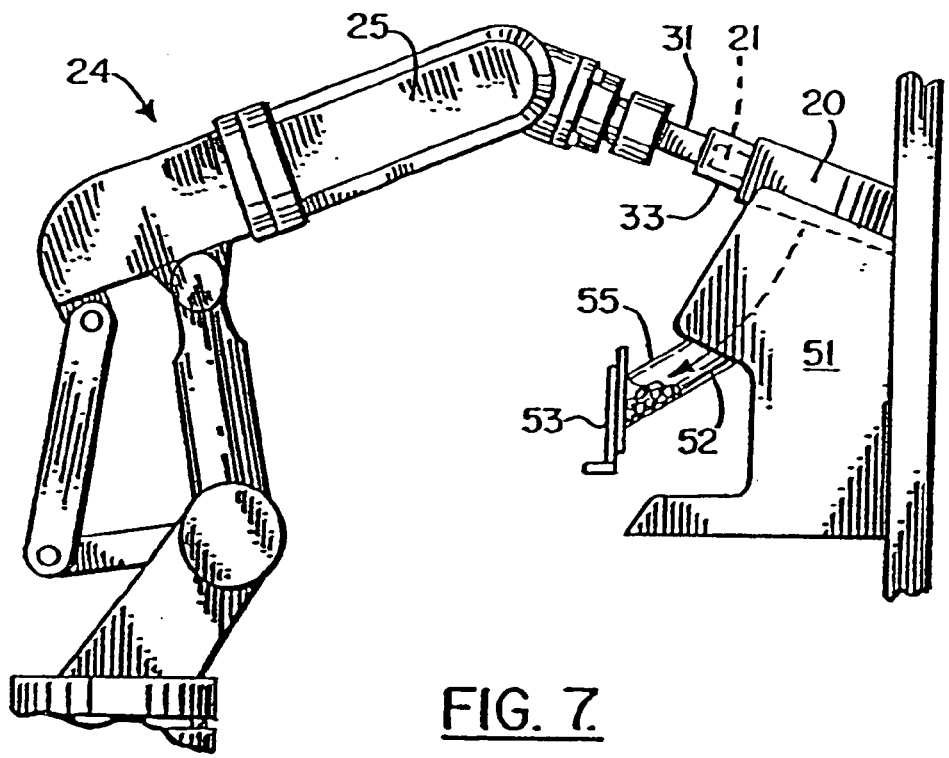
FIG. 7 is a fragmentary elevational view of the preferred embodiment of the apparatus of the present invention illustrating the placement of a bulk container on the counter/dispenser.

In FIG. 7, the robot arm is shown placing container 20 on counter/dispenser 51 so that pills can be dispensed therefrom. The counter/dispenser has a chute 52 for receiving pills that have been counted and dispensed from container 20. In FIG. 7, the pills 55 are shown contained within chute 52 after they have been dispensed from counter/dispenser 51.

Figure 10:
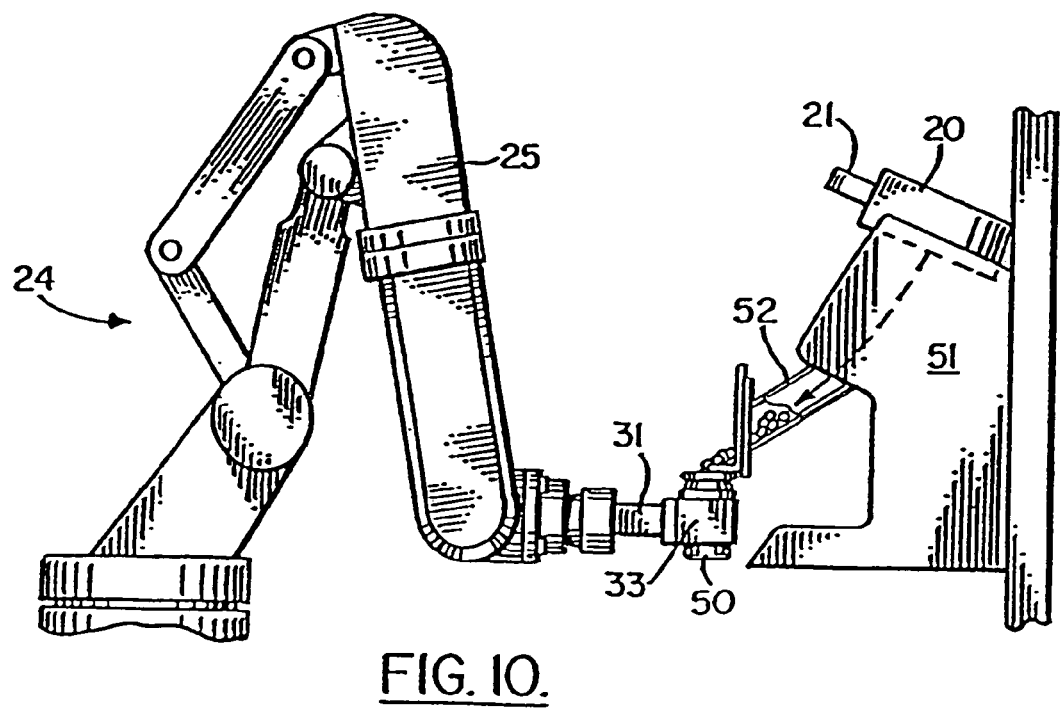
FIG. 10 is a fragmentary elevational view of the preferred embodiment of the apparatus of the present invention showing the dispensing of a selected number of pills from the counter/dispenser into a pill bottle that is supported by the robotic arm.

The counter/dispenser 51 can be provided with a door 53 that closes chute 52 so that the pills will be retained therein is shown in FIG. 7 until a pill bottle 50 is placed by robotic arm 25 in a position that opens the door 53 so that the pills will travel into the bottle as shown in FIG. 10.

Figure 9:
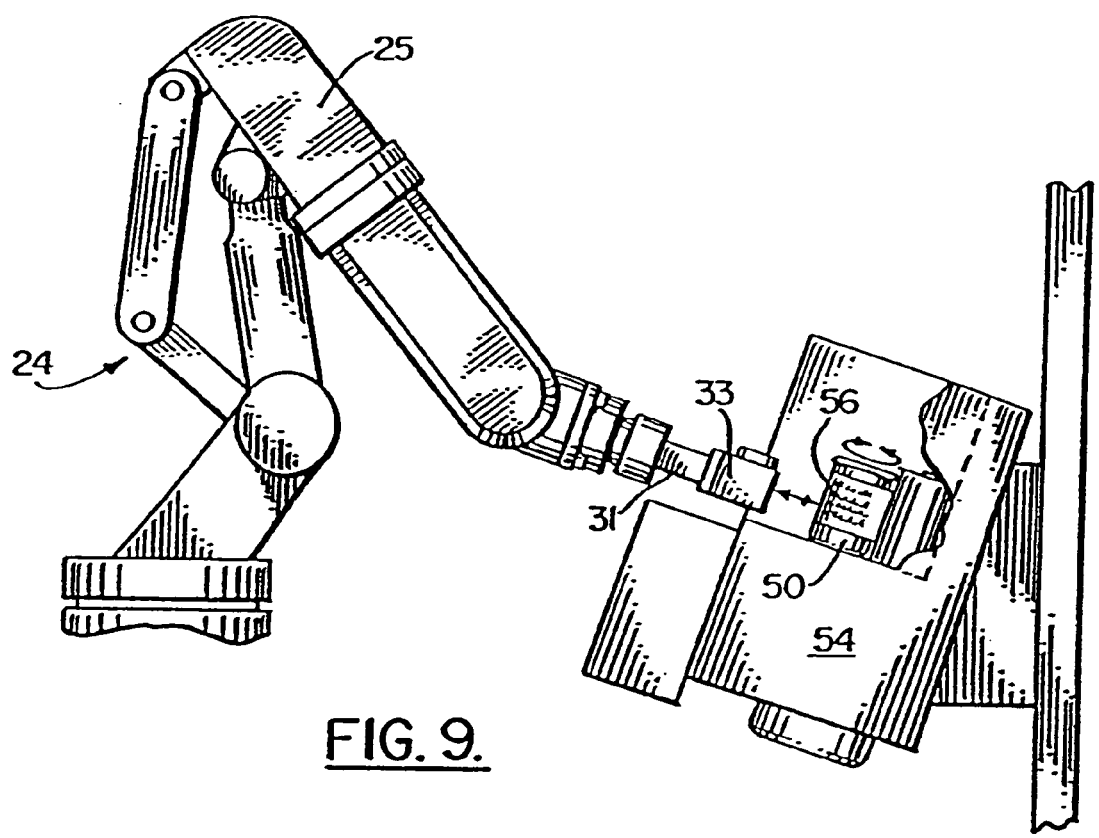
FIG. 9 is a fragmentary elevational view of the preferred embodiment of the apparatus of the present invention showing the robotic arm during the application of a label to the pill bottle at the label printer.

The computer 44 can also be used to control the placement of a label 56 on pill bottle 50 as shown in FIG. 9 using label printer 54 and label applier 64. The applicator is positioned near the output of the labeler. It includes a roller and clamp mechanism. The robot puts the vial on the roller. As the label exits the printer, the vial is rotated and the label is applied.

Figure 11:
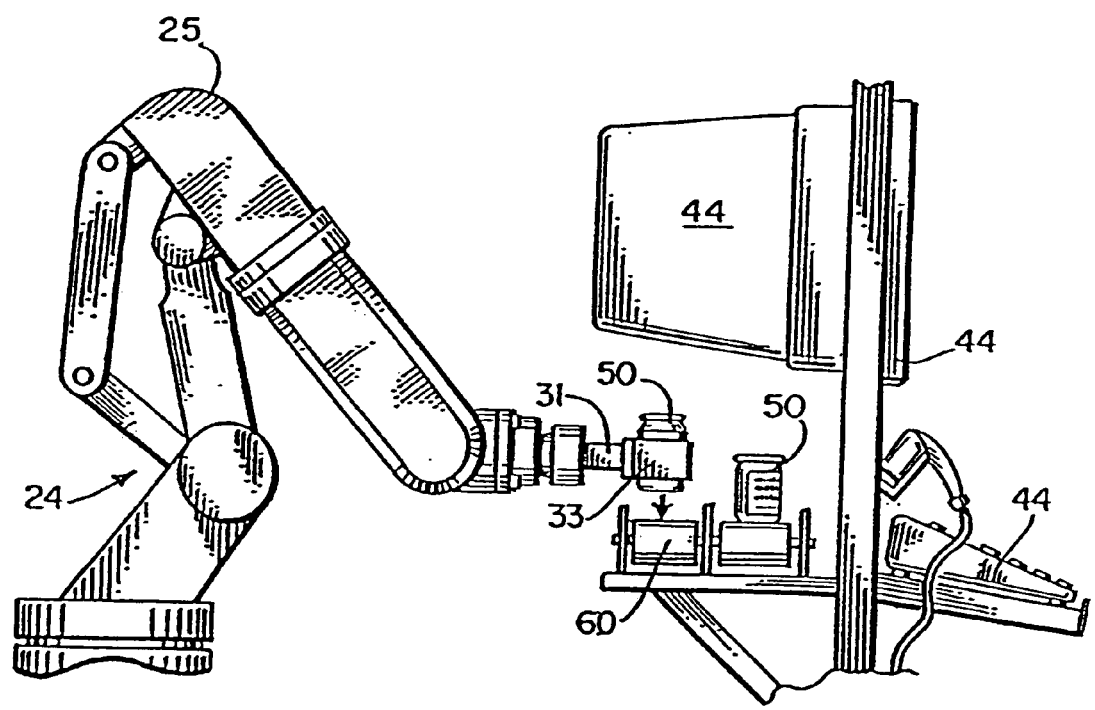
FIG. 11 is a fragmentary sectional elevational view of the preferred embodiment of the apparatus of the present invention showing the placement of a pill bottle on the conveyor after it has been filled with a selected number of pills.

After a pill bottle 50 has been filled with pill 55, it can be removed from the position shown in FIG. 10 and placed on a conveyor 60 as shown in FIG. 11. Vial conveyor 60 is used to transport the finished vials from the system enclosure.

The conveyor 60 is divided into at least two lanes. One lane is always used for "exception" vials and typically stops near the display and control unit. The other lanes are separately routed to remote destinations for the prescriptions such as "packing stations" of the model Pharmacy 2000 pill dispensing system, sold by APS, Inc. assignee of this application.

The conveyor 11 provides end portions 61, 62 and a wall 63 that retains a number of pill bottles 50 on the conveyor 60 until a druggist can remove them as shown in FIG. 6. This enables the druggist to control the computer 44 from console 11 and from that same position inspect each pill bottle 50, its label 56, and the pills 55 that have been dispensed thereinto to confirm that the prescription has in fact been properly filled.

Figure 8:
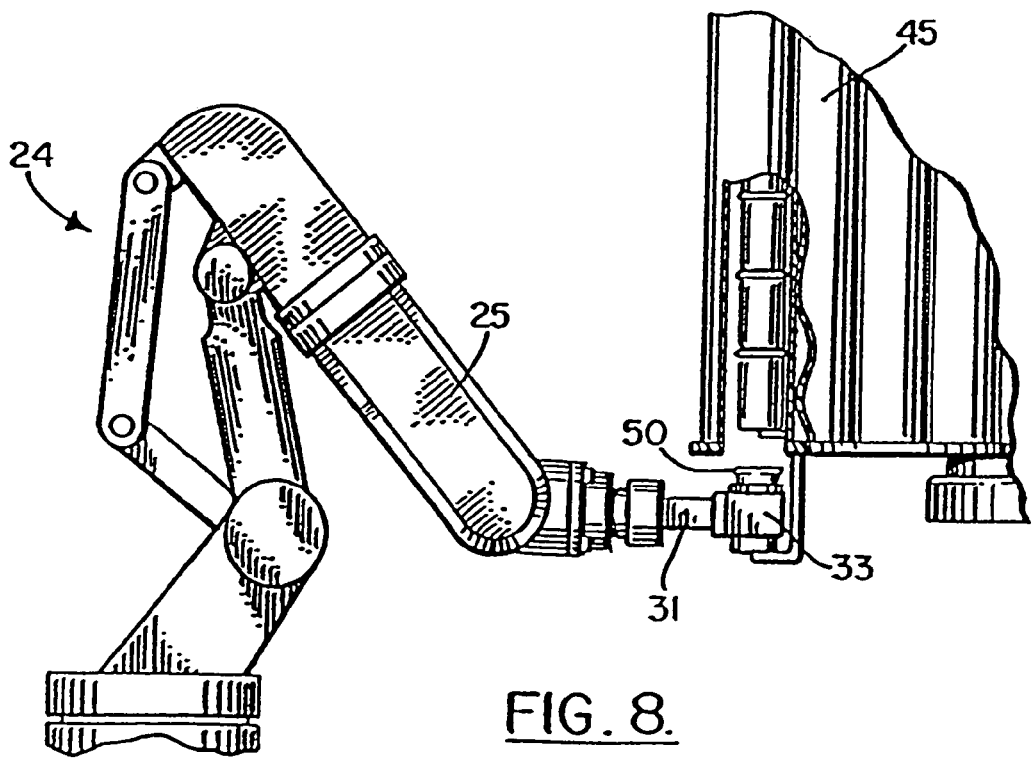
FIG. 8 is a fragmentary elevational view of the preferred embodiment of the apparatus of the present invention showing the removal of a pill bottle from the pill bottle dispenser by the robotic arm.
Figure 12:
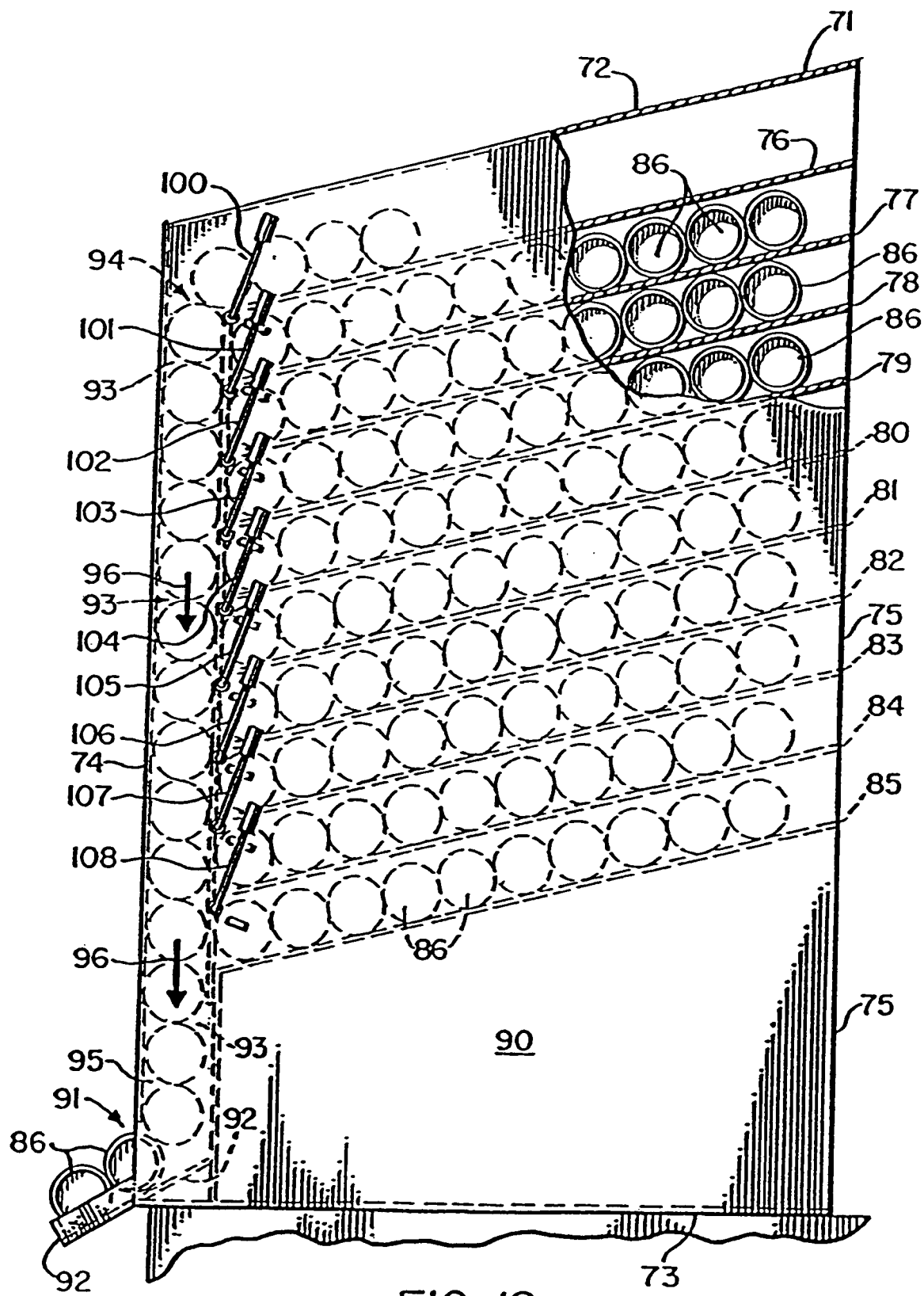
FIG. 12 is an elevational view of an alternate embodiment of the apparatus of the present invention showing the pill bottle dispenser portion thereof.

FIGS. 12-20 show an alternate embodiment of the apparatus of the present invention designated generally by the numeral 70 in FIG. 12. In FIG. 12, there is shown a bottle dispensing apparatus 70 that can be used in placed of the pill bottle dispenser 45 shown in FIGS. 1, 6-6A, and 8. In the alternate embodiment of FIGS. 12-20, the robot arm 25 grasps a pill bottle 86 from pill bottle dispenser 70 (see FIGS. 18-20) as an alternate to the removal of a pill bottle from dispenser 45 shown in FIG. 8. Otherwise, the pill bottle 86, once removed is used in the filling of a prescription as with the embodiment of FIGS. 1-11.

In FIG. 12, bottle dispensing apparatus 70 includes a frame 71 having an upper end 72 and a lower end 73. Frame 71 provides a front 74 that is generally planar and vertical and a rear 75 that is generally planar and vertical. A plurality of inclined plates 76-85 form a part of frame 71, the plate 76-85 being mounted in between side walls 89, 90 and connected thereto by welding, for example.

The plurality of inclined plates 76-85 enable a plurality of cylindrically-shaped pill bottles 86 to be stored on the inclined plates 76-85 as shown in FIG. 12. Because each of the plates 76-85 is inclined, the pill bottle 86 stored on each plate 76-85 roll toward the front 74 of frame 71 during use. At the front 74 of frame 71, there is provided a pair of spaced apart front panels 87, 88 with a gap therebetween. The front panels 87, 88 can simply be a continuation of side walls 89, 90 being formed integrally therewith. For example, the panels 87, 88 can simply be bent portions that are extensions of the side walls 89, 90 respectively.

Frame 71 provides a dispensing outlet 91 at the front 74 of frame 71 and at the lower end 73 of frame 71 as shown in FIGS. 12 and 18-20. Dispensing outlet 91 allows one cylindrically-shaped pill bottle 86 at a time to be dispensed from pill bottle dispenser 70. Delivery chute 91 extends in front of and below dispensing outlet 91 as shown in FIGS. 12 and 18-20. Delivery chute 92 has a pair of side walls 115, 116 and a pair of opposed stop portions 117, 118. The stop portions 117, 118 catch a bottle 86 after it has been dispensed so that it can be grabbed and removed by robotic arm 25 as shown in FIGS. 18-20.

During operation, the pill bottles 86 that are stored on the inclined plates 76-85 move toward the front 74 of frame 71 as pill bottles 86 are dispensed one at a time from dispensing outlet 91 and into delivery chute 92. In order to feed pill bottles 86 one at a time, a plurality of gates 100-108 are provided, each gate 100-108 being mounted respectively at the front end portion of an inclined plate 76-85 as shown in FIG. 12.

In addition to the plurality of gates 100-108, a dispensing channel 93 is provided that extends along the front 74 of frame 71. The dispensing channel 93 includes an upper end 94 and a lower end 95. The lower end 95 communicates with dispensing outlet 91. In FIG. 12, arrows 96 show the downward flow of pill bottles 86 during use and within the channel 93.

Figure 16:
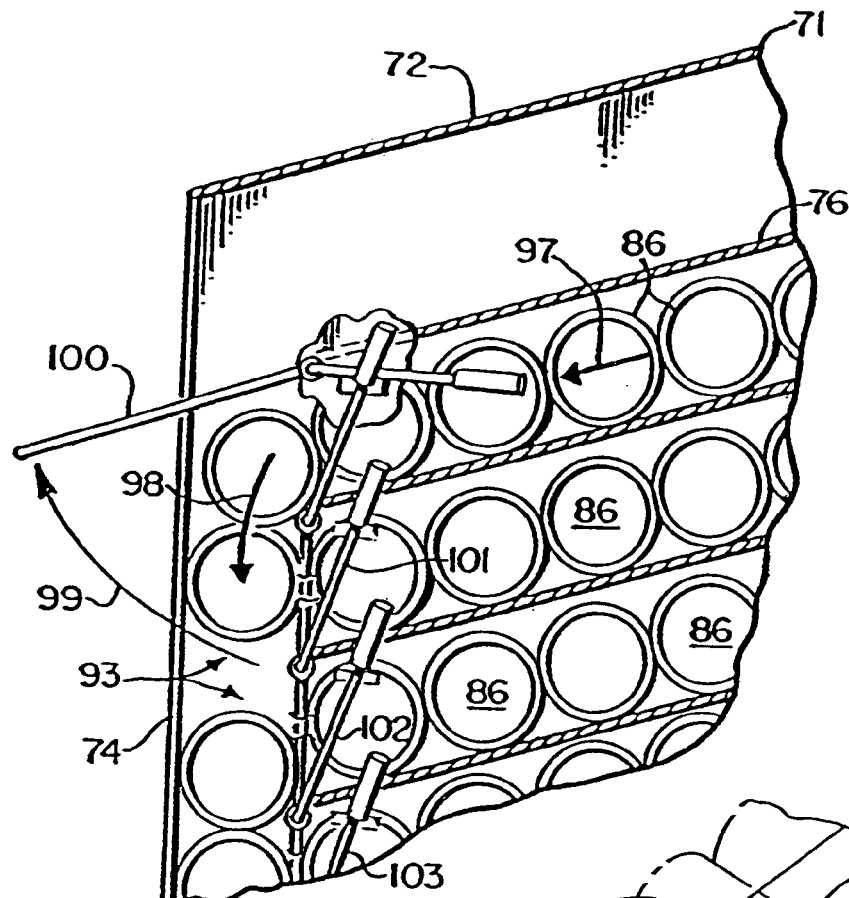
FIG. 16 is a partial elevational view of the alternate embodiment of the apparatus of the present invention showing movement of the gates.
Figure 17:
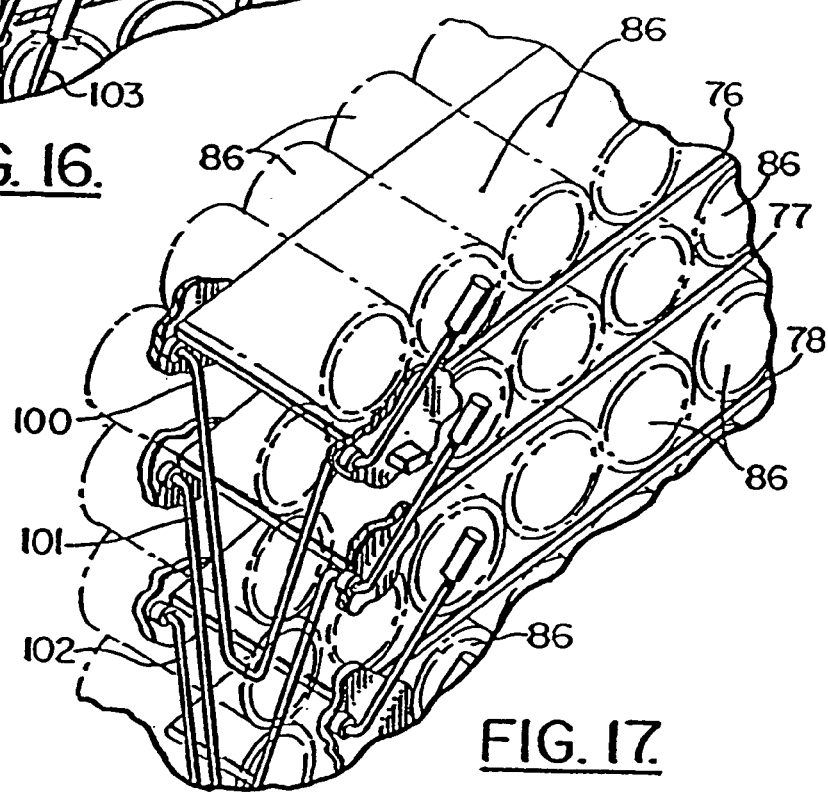
FIG. 17 is a partial perspective view of the alternate embodiment of the apparatus of the present invention.

In FIG. 13, arrow 97 shows the movement of bottles 86 toward channel 93 as they are moved by gravity toward the front 74 of frame 71 and eventually to channel 93. Arrow 98 in FIG. 16 illustrates the turn that a pill bottle 86 experiences when it leaves an inclined plate such as the plate 77 in FIG. 16 and enters channel 93. Curved arrow 99 in FIG. 16 illustrates the rotational movement of a gate 100 that occurs after all of the pill bottles 86 have been removed from two inclined plates 77, 78 that are immediately below the pivotal or rotary attachment of a gate 100 to frame 71.

Each of the gates 100-108 includes a counterweight 109 and a V-shaped portion 110. Further, a pair of spaced apart horizontal shafts 111, 112 are provided integrally with V-shaped portion 110. These horizontal shaft portions 111, 112 enable the gates 100-108 to be mounted to frame 71 using bearings 113 (for example, plastic sleeves). In FIGS. 18-20, the arrow 114 shows the turn that is made by pill bottles 86 that leave dispensing channel 93 and enter chute 92.

In FIGS. 13 and 14, the operation of the gates 100-108 can be seen. In FIG. 13, all of the inclined plates 76-85 are filled with bottles 86. As the bottles are dispensed from chute 92, the bottles from the highest inclined plate 73 that contains bottles 86 is emptied by the arrow 97 in FIG. 13. Once the bottles 86 on the inclined plate 76 are emptied, the bottles 86 contained in vertical dispensing channel 93 move downwardly. As soon as the bottles 86 in vertical dispensing channel 93 move downwardly below the bottom 119 of a particular gate 100-109, counterweight 109 rotates the gate into the open position as shown by arrow 99 in FIG. 16. When this occurs, the gate opens up the next row of pill bottles 86 contained on the next inclined plate that contains the bottles.

Each gate 100-108 opens in sequence, beginning with the gate 100 and ending with the gate 108. In the meantime, as each gate opens, the highest inclined plate 76 followed by the next highest inclined plate 77 dispenses its contents of pill bottles 86. The last inclined plate to dispense its bottles 86 is the lowest inclined plate 85. By the time the inclined plate 85 dispenses its bottles 86, bottles 86 contained in the vertical dispensing channel 93 will have moved below the bottom 119 of gate 108, namely, the lowest gate.

PARTS LIST

The following is a list of suitable parts and materials for the various elements of the preferred embodiment of the present invention.

| Part Number | Description |
| --- | --- |
| 10 | pill dispensing apparatus |
| 11 | console |
| 12 | shelving unit |
| 13 | column |
| 14 | top panel |
| 15 | bottom panel |
| 16 | rear panel |
| 17 | front surface |
| 18 | shelf |
| 19 | receptacle |
| 20 | bulk container |
| 21 | handle |
| 22 | side wall |
| 23 | side wall |
| 24 | robot |
| 25 | robotic arm |
| 25A | robotic arm |
| 25B | robotic arm |
| 26 | pedestal |
| 27 | vertical frame |
| 28 | horizontal support |
| 29 | arm segment |

-continued

| Part Number | Description |
| --- | --- |
| 30 | arm segment |
| 31 | free end portion |
| 32 | jaw |
| 33 | jaw |
| 34 | side wall |
| 35 | side wall |
| 36 | flat inside surface |
| 37 | flat inside surface |
| 38 | horizontal plate |
| 39 | horizontal plate |
| 40 | frame |
| 41 | feet |
| 42 | arrow |
| 43 | arrow |
| 44 | computer |
| 45 | pill bottle dispenser |
| 46 | arcuate surface |
| 47 | arcuate surface |
| 48 | curved wall |
| 49 | curved wall |
| 50 | pill bottle |
| 51 | counter/dispenser |
| 52 | chute |
| 53 | door |
| 54 | label printer |
| 55 | pills |
| 56 | label |
| 60 | conveyor |
| 61 | end |
| 62 | end |
| 63 | wall |
| 64 | label applier |
| 65 | bar code scanner |
| 66 | replenish out port |
| 67 | replenish in port |
| 70 | bottle dispensing apparatus |
| 71 | frame |
| 72 | upper end |
| 73 | lower end |
| 74 | front |
| 75 | rear |
| 76 | inclined plate |
| 77 | inclined plate |
| 78 | inclined plate |
| 79 | inclined plate |
| 80 | inclined plate |
| 81 | inclined plate |
| 82 | inclined plate |
| 83 | inclined plate |
| 84 | inclined plate |
| 85 | inclined plate |
| 86 | cylindrically-shaped bottles |
| 87 | front panel |
| 88 | front panel |
| 89 | side wall |
| 90 | side wall |
| 91 | dispensing outlet |
| 92 | delivery chute |
| 93 | dispensing channel |
| 94 | upper end channel |
| 95 | lower end channel |
| 96 | arrow |
| 97 | arrow |
| 98 | arrow |
| 99 | curved arrow |
| 100 | gate |
| 101 | gate |
| 102 | gate |
| 103 | gate |
| 104 | gate |
| 105 | gate |
| 106 | gate |
| 107 | gate |
| 108 | gate |
| 109 | counterweight |
| 110 | V-shaped portion |
| 111 | horizontal shaft |

-continued

| Part Number | Description |
|---|---|
| 112 | horizontal shaft |
| 113 | bearing |
| 114 | arrow |
| 115 | side wall |
| 116 | side wall |
| 117 | stop |
| 118 | stop |

The foregoing embodiments are presented by way of example only; the scope of the present invention is to be limited only by the following claims.

That which is claimed:

1. An apparatus for filling prescriptions, comprising: a plurality of containers storing respective types of pills; a vial storage device for storing a plurality of vials; a counting and dispensing unit; and a computer controlled robot configured to automatically retrieve respective containers and move the respective containers to said counting and dispensing unit, said computer controlled robot also configured to move vials from said vial storage device to said counting and dispensing unit and from said counting and dispensing unit to a discharge location.

2. The apparatus of claim 1 further comprising a label printing and applying unit, and wherein said computer controlled robot automatically moves vials from said vial storage device, to said label printing and applying unit, and then to said counting and dispensing unit.

3. The apparatus of claim 1 wherein said vial storage device comprises a dispenser.

4. The apparatus of claim 1 wherein said robot includes an articulated, computer controlled arm.

5. The apparatus of claim 1 wherein a free end of said robot includes first and second gripping surface portions that are movable relative to one another and that are configured to grip a selected container or a selected vial, respectively.

6. The apparatus of claim 1 further comprising replenishment in and replenishment out ports, and wherein said computer controlled robot is configured to automatically move said containers from and to the replenishment in and replenishment out ports, respectively.

7. An apparatus for filling prescriptions, comprising: a plurality of containers storing respective types of pills; a vial storage device for storing a plurality of vials; a label applying unit; a counting and dispensing unit; and a computer controlled robot configured to automatically retrieve respective containers and move the respective containers to said counting and dispensing unit, said computer controlled robot also configured to move vials from said vial storage device to said label applying unit and then to said counting and dispensing unit.

8. The apparatus of claim 7 wherein said vial storage device comprises a dispenser.

9. The apparatus of claim 7 wherein said robot includes an articulated, computer controlled arm.

10. The apparatus of claim 7 wherein a free end of said robot includes first and second gripping surface portions that are movable relative to one another and that are configured to grip a selected container or a selected vial, respectively.

11. An apparatus for filling prescriptions, comprising: a plurality of containers storing respective types of pills; a vial storage device for storing a plurality of vials; a counting and dispensing unit; a computer controlled robot configured to automatically retrieve respective containers and move the respective containers to said counting and dispensing unit, said computer controlled robot also configured to move vials from said vial storage device to said counting and dispensing unit and from said counting and dispensing unit to a discharge location; and an off load device proximate the discharge location, wherein said off-load device comprises one of a conveyor and a carousel.

12. The apparatus of claim 11 wherein said off-load device comprises a conveyor having more than one lane.

13. An apparatus for filling prescriptions, comprising: a plurality of containers storing respective types of pills; a vial storage device for storing a plurality of vials; a counting and dispensing unit; a computer controlled robot configured to automatically retrieve respective containers and move the respective containers to said counting and dispensing unit, said computer controlled robot also configured to move vials from said vial storage device to said counting and dispensing unit and from said counting and dispensing unit to a discharge location; and an off-load device proximate the discharge location, wherein said off load device comprises one of a conveyor and a carousel;
further comprising replenishment in and replenishment out ports, and wherein said computer controlled robot is configured to automatically move said containers from and to the replenishment in and replenishment out ports, respectively.

14. An apparatus for filling prescriptions, comprising: a plurality of containers storing respective types of pills; a vial storage device for storing a plurality of vials; a label applying unit; a counting and dispensing unit; a computer controlled robot configured to automatically retrieve respective containers and move the respective containers to said counting and dispensing unit, said computer controlled robot also configured to move vials from said vial storage device to said label applying unit and then to said counting and dispensing unit; and an off-load device, wherein said robot is further configured to move vials from said counting and dispensing unit to said off load device, and wherein said off-load device comprises one of a conveyor and a carousel.

15. The apparatus of claim 14 further comprising replenishment in and replenishment out ports, and wherein said computer controlled robot is configured to automatically move said containers from and to the replenishment in and replenishment out ports, respectively.

* * * * *